United States Patent [19]

Kato et al.

[11] Patent Number: 5,240,616
[45] Date of Patent: Aug. 31, 1993

[54] LIQUID CHROMATOGRAPH-DIRECT COUPLED MASS SPECTROMETER

[75] Inventors: Yoshiaki Kato, Mito; Tadao Mimura, Katsuta, both of Japan

[73] Assignee: Hitachi, Ltd., Tokyo, Japan

[21] Appl. No.: 492,321

[22] Filed: Mar. 12, 1990

Related U.S. Application Data

[63] Continuation of Ser. No. 340,687, Apr. 20, 1989, abandoned.

[30] Foreign Application Priority Data

Apr. 22, 1988 [JP] Japan .................................. 63-99366

[51] Int. Cl.$^5$ ............................................. B01D 15/08
[52] U.S. Cl. ................................ 210/656; 210/198.2; 250/288; 422/70
[58] Field of Search ............ 210/635, 656, 659, 198.2; 422/70; 250/288 A; 73/61.1 C

[56] References Cited

U.S. PATENT DOCUMENTS

| | | | |
|---|---|---|---|
| 4,298,795 | 11/1981 | Takeuchi | 250/288 A |
| 4,570,068 | 2/1986 | Sakairi | 250/288 A |
| 4,607,163 | 8/1986 | Mizuno | 250/288 A |
| 4,667,100 | 5/1987 | Lagna | 250/288 A |
| 4,687,929 | 8/1987 | Browner | 250/288 A |
| 4,708,782 | 11/1987 | Andresen | 250/288 A |
| 4,740,298 | 4/1988 | Andresen | 250/288 A |
| 4,762,995 | 8/1988 | Browner | 250/288 A |

FOREIGN PATENT DOCUMENTS

2151021 7/1985 United Kingdom ............. 210/198.2

OTHER PUBLICATIONS

Corey, "Liquid Chromatography/Mass Spectrometry," Anal. Chem., vol. 58. No. 14, pp. 1451A–1461A, Dec. 1986.
Karger, "On-line Reversed Phase Liquid Chromatography—Mass Spectrometry", Anal. Chem. vol. 51, No. 14, pp. 2324–2328, Dec. 1979.
Games, Continuous Flow Fast Bombardment Liquid Chromatography/Mass Spectrometry, Biomedical and Environmental Mass Spectrometry, vol. 15, pp. 179–182 (1988).
Apfell Gas-Nebulized Direct Liquid Introduction Interface for Liquid Chromatography/Mass Spectrometry, Anal. Chem. vol. 55, pp. 2280–2284 Dec. 1983.
Tsuge, "Vacuum Nebulizing Interface for Direct Coupling of Micro–Liquid Chromatograph and Mass Spectrometer Analytical Chemistry", vol. 51, No. 1, Jan. 1979, pp. 166–169.
Hirata, "The Application of a New Sampling Technique" Organic Mass Spectrometry, vol. 14, No. 3, 1979, pp. 126–128.

*Primary Examiner*—Ernest G. Therkorn
*Attorney, Agent, or Firm*—Antonelli, Terry, Stout & Kraus

[57] ABSTRACT

A liquid chromatograph-direct coupled mass spectrometer, which comprises a liquid chromatograph section, a mass spectrometer section and an interface section coupling the liquid chromatograph section with the mass spectrometer section, the interface section being provided with a first nebulizing means for nebulizing an eluate of a hydrophobic solvent containing a sample in solution introduced from the liquid chromatograph section through a capillary continuously into a vacuum or atmospheric pressure region and the first nebulizing means being further provided with a second nebulizing means for nebulizing a hydrophilic solvent and with a heating means for heating the first and second nebulizing means has a high separability and has no limit to selection of a mobile phase solvent and an ionization solvent.

10 Claims, 2 Drawing Sheets

LIQUID CHROMATOGRAPH-DIRECT COUPLED MASS SPECTROMETER

This application is a continuation of application Ser. No. 07/340,687, filed on Apr. 20, 1989, now abandoned.

BACKGROUND OF THE INVENTION

This invention relates to a liquid chromatograph-direct coupled mass spectrometer, which will be hereinafter referred to as LC/MS, and more particularly to a liquid inlet port in the interface of the LC/MS, which is suitable for improving the ionization efficiency without impairing the separation condition of liquid chromatography.

What is important in an LC/MS is how to introduce a sample into the mass spectrometer without impairing the separation ability in the liquid chromatography. Thus, it is desirable that an LC/MS can perform measurements without changing the measurement conditions of liquid chromatography. In an LC/MS using an ionization system based on ion-molecule reactions, however, some species of solutes in a mobile phase solvent of liquid chromatography cannot be ionized in some cases. Generally, ionization based on ion-molecule reaction under a pressure from the atmospheric pressure to a vacuum of about 1 Torr includes several types of reactions. That is, proton transfer reaction and ion clustering reaction (addition reaction) take place as principal types of reactions in the ionization.

Mobile phase solvent molecules A are ionized by corona discharge and electron bombardments and formed into reagent gas ions, i.e. $AH^+$ ions through further collisions further with neutral molecules. Then, $AH^+$ ions further collide with solute molecules B, whereby protons $H^+$ are transferred from the $AH^+$ ions to the solute molecules B to ionize the solute molecules B according to the following reaction equation.

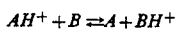

$$AH^+ + B \rightleftarrows A + BH^+$$

This proton transfer reaction has a high reaction rate and is one of the most important reactions taking part in the chemical ionization. In order to make the reaction proceed toward the right side in the foregoing reaction equation, the proton affinity of mobile phase solvent molecules A must be lower than that of solute molecules B, whereby the protons $H^+$ can be smoothly transferred from A to B. In order to efficiently ionize B, a larger difference in the proton affinity is desirable between the mobile phase solvent molecules A and the solute molecules B. Proton affinity of solvents often used in liquid chromatography is 173.7 kcal/mole with $H_2O$, 186.5 kcal/mole with methanol and 191.4 kcal/mole with acetonitrile. If the proton affinity of solute molecules B is more than 191.4 kcal/mole, ionization can proceed efficiently with any of these solvents, whereas in case of solute molecules B having a proton affinity of, for example, 190 kcal/mole, ionization can proceed with water or methanol as a mobile phase solvent, but not with acetonitrile. Thus, it is necessary in the chemical ionization to check the proton affinities of mobile phase solvent molecules A and the solute molecules B. In liquid chromatography, however, the mobile phase solvent plays a role of separating solutes and thus free selection of mobile phase solvents to improve the ionization efficiency is very limited. That is, generally it is not possible to simply replace acetonitrile with water as a mobile phase solvent because the ionization cannot be carried out with acetonitrile. In order to solve this problem, it has been proposed to use an optimum mobile phase solvent playing role of separating solute components in a liquid chromatography, add another solvent suitable for ionizing separated solute components and feed the resulting mixture to a nebulizing means [Anal Chem. 51 No. 14, 2324-2326 (1979); Biochemical and Environmental Mass Spectroscopy, Vol. 15, 179-182 (1988)].

FIG. 1 shows a conventional system for nebulizing an eluate in an LC/MS, where a mobile phase solvent as an eluent, stored in an eluent storage tank 1 is fed to a separation column 4 through a sample injector 3 by driving a pump 2. A sample in a solution form is injected into the eluent at the sample injector 3 and separated into solute components through the separation column 4. When the eluent is not suitable for the ionization, the eluate from the separation column 4 is led to a mixing column 5 provided downstream of the separation column 4, where the eluate is mixed with an ionization solvent fed from an ionization solvent storage tank 6 by driving a pump 2'. The mixing column 5 is filled with glass beads, and the resulting-mixture is led to a nebulizing means. However, in the proposed art, the separated solute components in the eluate from the separation column 4 are diffused and remixed in the mixing column 5, forming the so-called dead volumes. Thus, no satisfactory separation is expected. Furthermore, it is a premise of the proposed art that the mobile phase solvent and the ionization solvent are well mutually miscible and thus there is a limit to selection of an ionization solvent. For example, in the case of hexane as a mobile phase solvent, water cannot be used as an ionization solvent.

Recently, a nebulizing means for the interface region of LC/MS using a thermospray system or an atmospheric pressure ionization (API) system has been proposed to attain direct and rapid vaporization of an eluate from the liquid chromatograph and successive ionization reactions [Anal Chem, 58 No. 14 1451A-1461A (1986); Anal Chem, 55, 2280-2284 (1983)]. However, the proposed nebulizing art still has such problems as use of auxiliary gases such as nebulizer gas and makeup gas in the vaporization of eluate, and consequent unstable ionization reactions and poor separation ability in the mass spectroscopy.

SUMMARY OF THE INVENTION

An object of the present invention is to provide a liquid chromatograph-direct coupled mass spectrometer having a high separation ability without any limit to selection of mobile phase solvent and ionization solvent and free from the disadvantages of the prior art.

The object of the present invention can be attained by a liquid chromatograph-direct coupled mass spectrometer, which comprises a liquid chromatograph section, a mass spectrometer section and an interface section coupling the liquid chromatograph section with the mass spectrometer section, the interface section being provided with a first nebulizing means for nebulizing an eluate of a hydrophobic solvent containing a sample in solution introduced from the liquid chromatograph section through a capillary continuously into a vacuum or atmospheric pressure region and the first nebulizing means being further provided with a second nebulizing means for nebulizing a hydrophilic solvent and with a heating means for heating the first and second nebulizing means.

In the present invention, the hydrophobic solvent (mobile phase solvent) containing a sample in solution and the hydrophilic solvent (ionizing solvent) are vaporized by the heating means and mixed together in a gaseous state, and thus the mutually immiscible solvents can be mixed. Furthermore, no such mixing column or no such auxiliary gases as nebulizer gas and makeup gas is required and thus satisfactory separation ability can be obtained.

PREFERRED EMBODIMENTS OF THE INVENTION

Figure 2:
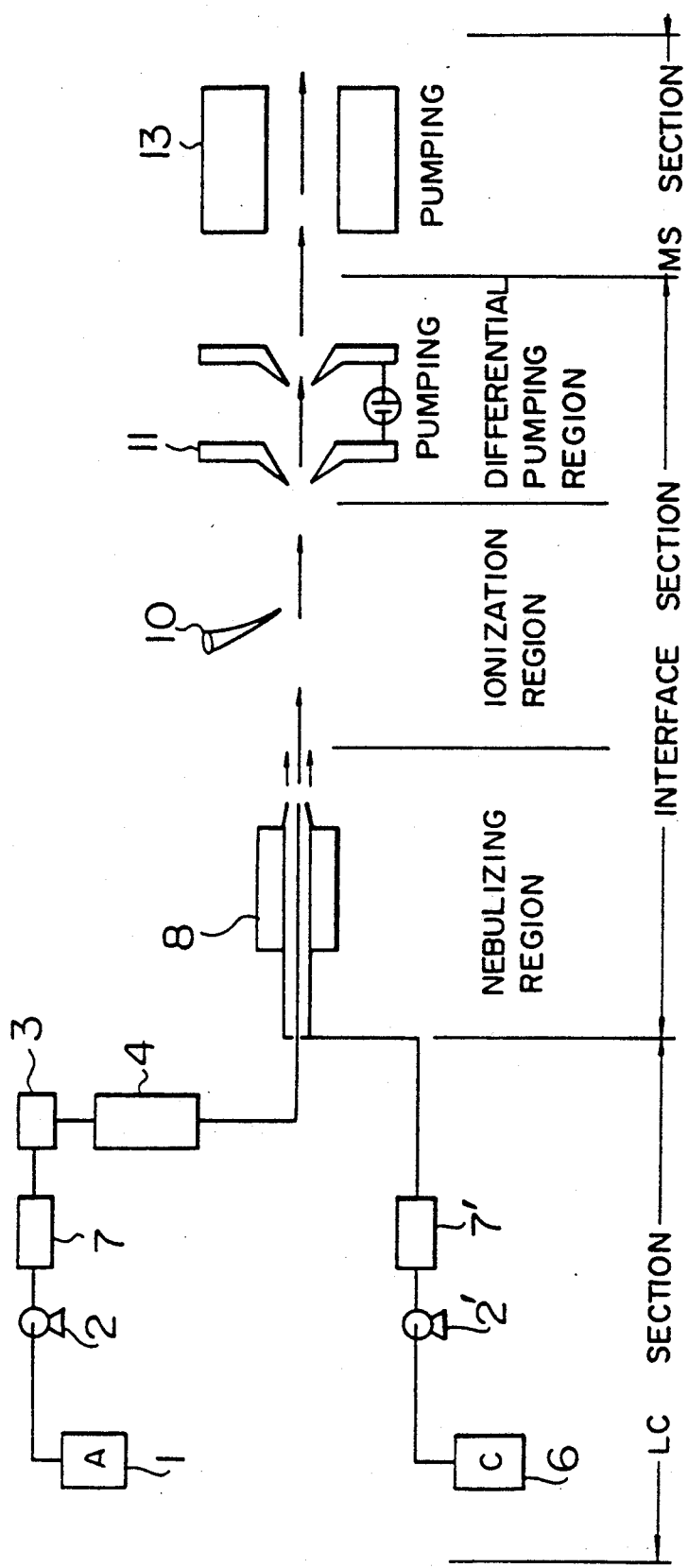
FIG. 2 is a schematic flow diagram of LC/MC according to one embodiment of the present invention.

In FIG. 2, one embodiment of LC/MS according to the present invention is shown, which comprises a liquid chromatograph section, an interface section and a mass spectrometer section.

In FIG. 2, a hydrophobic solvent A (eluent) as a mobile phase solvent, stored in an eluent storage tank 1 is fed to a separation column 4 through a damper 7 and a sample injector 3 by driving a pump 2. A sample is injected into the eluent at the sample injector 3 and separated into solute components in the separation column 4 and an eluate containing the separated solute components from the separation column 4 is led to a nebulizer 8 through a capillary (inner diameter: 0.1–0.2 mm).

On the other hand, a hydrophilic solvent C as an ionization solvent, stored in an ionization solvent tank 6, is led to the nebulizer 8 through a damper 7' by driving a pump 2'.

Figure 1:
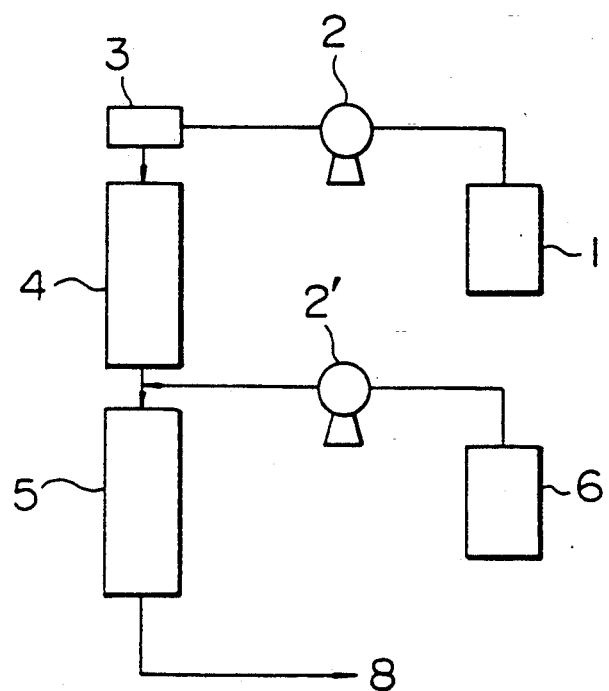
FIG. 1 is a schematic flow diagram showing an example of liquid chromatograph section in LC/MS according to the prior art.
Figure 3:
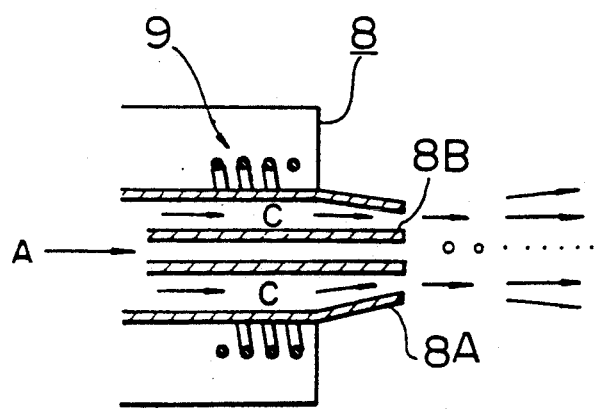
FIG. 3 is a detailed view of a nebulizer shown in FIG. 2.

As shown in FIG. 3, the nebulizer 8 comprises a nozzle 8B, to which the eluate from the separation column 4 is led through the capillary, and a nozzle 8A having a larger diameter than that of the nozzle 8B, provided coaxially with the nozzle 8B, and the ionization solvent C from the ionization solvent tank 6 is led to the passage formed between the outer wall of the nozzle 8B and the inner wall of the nozzle 8A.

A heater 9 is provided at the outer periphery of the nozzle 8A to heat the nozzles 8A and 8B to a temperature of about 200° to about 600° C. The ionization solvent C from the ionization solvent tank 6 is thus heated and vaporized by heating with the heater 9 and injected into a vacuum or atmospheric pressure region from the passage between the inner wall of nozzle 8A and the outer wall of nozzle 8B. At the same time, the eluate from the separation column 4 is heated and nebulized and injected into the same region as above from the nozzle 8B. The nebulized liquid droplets of eluate collide with molecules of the heated and vaporized ionization solvent C and are made finer and ultimately vaporized. Thus, the eluate and the ionization solvent C can be completely mixed in a mutually gaseous state, whereby the hydrophobic solvent as a mobile phase solvent and the hydrophilic solvent as an ionization solvent, which are mutually immiscible in a liquid state, can be completely mixed.

Furthermore, the vaporized ionization solvent C in a gaseous state guides the nebulized eluate A into the desired direction and also acts to make the droplets of the eluate A finer, that is, plays a role of so-called makeup gas. Thus, the swing of ions to be detected in the mass spectrometer section can be made smaller.

Then, the mixed gas of the vaporized eluate A and the ionization solvent C is ionized by a corona discharge needle 10 in an ionization region, passed through apertures at partition walls 11 and 11' in a differential pumping region and mass analyzed in a mass spectrometer section with quadrupoles 13.

In the foregoing embodiment, the nozzles 8B and 8A in the nebulizer 8 are in a coaxial double pipe structure, but are not always limited thereto. That is, the nozzle 8B and nozzle 8A are provided in different axial directions from each other and their outlets are positioned close to each other to be focused to one point.

The foregoing nebulizer is applicable to a thermospray system or API system.

As is apparent from the foregoing description, the present LC/MC has a high separation ability without any limit to selection of hydrophobic solvents and hydrophilic solvents.

What is claimed is:

1. A method of using a liquid chromatograph-direct coupled mass spectrometer, the spectrometer comprising a liquid chromatograph section, a mass spectrometer section and an interface section coupling the liquid chromatograph section with the mass spectrometer section; a source of hydrophilic solvent, with means for passing the hydrophilic solvent to the interface section without passing through the liquid chromatograph section; and a source of hydrophobic solvent, with means for passing the hydrophobic solvent, together with a sample, to the liquid chromatograph section, and with means for passing a liquid eluate from the liquid chromatograph section to the interface section; the interface section being provided with a nebulizing means for nebulizing the liquid eluate of the hydrophobic solvent containing the sample in solution introduced from the liquid chromatograph section through a capillary continuously into a vacuum or atmospheric pressure region, and with a vaporizing means for vaporizing the liquid hydrophilic solvent, the interface section further being provided with a heating means for heating the nebulizing means and vaporizing means in order to vaporize the liquid hydrophilic solvent and to heat the liquid eluate, whereby the hydrophobic solvent and hydrophilic solvent can be mixed together without a mixing column and without auxiliary gases, the method comprising the steps of:

passing the hydrophobic solvent, from the source thereof, and with the sample therein, to the liquid chromatograph section, where the shape is separated into solute components;

passing liquid eluate from the liquid chromatograph section to the interface section;

passing the hydrophilic solvent from a source thereof to the interface section, without passing the hydrophilic solvent through the liquid chromatograph section; and in the interface section, passing the liquid eluate of the hydrophobic solvent containing the sample in solution through said nebulizing means so as to nebulize the liquid eluate, introduced from the liquid chromatograph section through said capillary continuously into a vacuum or atmospheric pressure region, and vaporizing the liquid hydrophilic solvent in said vaporizing means, the liquid eluate being heated and the liquid hydrophilic solvent being vaporized by using said heating means to heat the nebulizing means and vaporizing means.

2. A method of performing mass analysis through use of a liquid chromatograph-direct coupled mass spectrometer, comprising the steps of:
   (a) passing a sample, in an eluent, through a separation column so as to separate the sample into separated components in a liquid eluate;
   (b) passing the liquid eluate, containing the separated components of the sample, to a nebulizer in a nebulizer region of the liquid chromatograph-direct coupled mass spectrometer;
   (c) nebulizing the liquid eluate in the nebulizer;
   (d) vaporizing a liquid ionization solvent in the nebulizer region;
   (e) combining the vaporized ionization solvent and nebulized liquid eluate, the nebulized liquid eluate being vaporized, the vaporized ionization solvent and vaporized eluate being mixed in a mutually gaseous state; and
   (f) passing the mixture of vaporized ionization solvent and vaporized eluate to a mass spectrometer so as to perform mass analysis.

3. A method of performing mass analysis according to claim 2, wherein the eluent is a hydrophobic solvent, and the ionization solvent is a hydrophilic solvent.

4. A method of performing mass analysis according to claim 2, wherein the liquid ionization solvent is heated, so as to vaporize the ionization solvent, in the nebulizer region; and wherein the vaporized ionization solvent, at a temperature sufficiently high to vaporize the nebulized liquid eluate, is combined with the nebulized liquid eluate so as to vaporize the nebulized liquid eluate.

5. A method of performing mass analysis according to claim 4, wherein the eluent is a hydrophobic solvent, and the ionization solvent is a hydrophilic solvent.

6. A method of performing mass analysis according to claim 2, wherein, in combining the vaporized ionization solvent and nebulized liquid eluate, the nebulized liquid eluate is vaporized by the vaporized ionization solvent.

7. A method of mixing an eluate, containing a sample component, and an ionization solvent, prior to passing the eluate to a mass spectrometer in using a liquid chromatograph-direct coupled mass spectrometer, comprising the steps of:
   (a) passing the eluate, as a liquid, to a nebulizer, in a nebulizer region of the liquid chromatograph-direct coupled mass spectrometer;
   (b) nebulizing the liquid eluate in the nebulizer;
   (c) vaporizing the ionization solvent in the nebulizer region; and
   (d) combining the vaporized ionization solvent and nebulized liquid eluate, the nebulized liquid eluate being vaporized, the vaporized ionization solvent and vaporized eluate being mixed in a mutually gaseous state.

8. A method according to claim 7, wherein the eluate includes a hydrophobic solvent, and the ionization solvent is a hydrophilic solvent, the hydrophobic and hydrophilic solvents being mixed in the mutually gaseous state.

9. A method according to claim 7, wherein the liquid ionization solvent is heated, so as to vaporize the liquid ionization solvent, in the nebulizer region; and wherein the vaporized ionization solvent, at a temperature sufficiently high to vaporize the nebulized liquid eluate, is combined with the nebulized liquid eluate so as to vaporize the nebulized liquid eluate.

10. A method according to claim 9, wherein the eluate includes a hydrophobic solvent, and the ionization solvent is a hydrophilic solvent, the hydrophobic and hydrophilic solvents being mixed in the mutually gaseous state.

* * * * *